(12) United States Patent
Yazdi

(10) Patent No.: US 8,182,504 B2
(45) Date of Patent: May 22, 2012

(54) NASAL DILATOR AND USES THEREOF

(75) Inventor: Alexandre Yazdi, Saint-Denis (FR)

(73) Assignee: Sibiotech, Paris (FR)

( * ) Notice: Subject to any disclaimer, the term of this patent is extended or adjusted under 35 U.S.C. 154(b) by 694 days.

(21) Appl. No.: 11/630,895

(22) PCT Filed: Jun. 28, 2005

(86) PCT No.: PCT/FR2005/001634
§ 371 (c)(1), (2), (4) Date: Dec. 27, 2006

(87) PCT Pub. No.: WO2006/010848
PCT Pub. Date: Feb. 2, 2006

(65) Prior Publication Data
US 2008/0119885 A1   May 22, 2008

(30) Foreign Application Priority Data
Jun. 28, 2004   (FR) ...................................... 04 07085

(51) Int. Cl.
*A61M 29/00* (2006.01)
(52) U.S. Cl. ...................................................... 606/199
(58) Field of Classification Search ................ 606/199, 606/204.45, 196, 204.15; 128/848, 200.24; 602/902
See application file for complete search history.

(56) References Cited

U.S. PATENT DOCUMENTS

| | | | | |
|---|---|---|---|---|
| 1,034,123 A | * | 7/1912 | Knowlson | 606/199 |
| 5,479,944 A | * | 1/1996 | Petruson | 128/858 |
| 5,499,065 A | * | 3/1996 | Zimmerman | 351/200 |
| 5,922,006 A | * | 7/1999 | Sugerman | 606/204.45 |
| 2002/0000227 A1 | | 1/2002 | Duyke et al. | |
| 2002/0177871 A1 | | 11/2002 | Santin | |
| 2003/0150449 A1 | | 8/2003 | Spinelli et al. | |
| 2004/0111109 A1 | * | 6/2004 | Ruiz | 606/199 |

FOREIGN PATENT DOCUMENTS

| | | |
|---|---|---|
| FI | 1 351 537 | 2/1964 |
| FR | 1 351 537 | 12/1962 |
| JP | 10323362 | 12/1998 |
| WO | 00/66048 | 11/2000 |

* cited by examiner

*Primary Examiner* — Ryan Severson
*Assistant Examiner* — Tin Nguyen
(74) *Attorney, Agent, or Firm* — Young & Thompson

(57) ABSTRACT

A mechanical nasal dilator includes a frame provided with support plates (6,6') at its ends, the frame including a central extranasal portion (1) and two intranasal portions (2,2'), wherein the extranasal portion (2) of the frame is globally U-shaped, whereof the central portion is elastic and spaces apart the nose wings by spring effect, the end of each of the branches of the U being itself U-shaped whereof one branch forms one part of the extranasal portion of the frame and the other branch, located between the branches of the extranasal portion of the frame, forms the intranasal portions (2,2').

13 Claims, 1 Drawing Sheet

NASAL DILATOR AND USES THEREOF

BACKGROUND OF THE INVENTION

The present invention relates to a nasal dilator and its applications.

DESCRIPTION OF THE RELATED ART

Human nasal breathing (10 000 to 15 000 liters of air/day) has essential functions, amongst others of warming and humidifying the air, before it reaches the lungs. Its obstruction is therefore harmful and uncomfortable, more particularly during sleep.

The partial or total closure of the nasal respiratory tract may have different origins. Infectious and allergic rhinosinusitises are the most frequent, on average two episodes/year in adults. They form the most frequent medical afflication, responsible for the highest rate of school and work absenteeism with self-medication in 70% of patients. In the USA, their cost is greater than 6 billion dollars per year. Chronic rhinosinusitis (CRS) is the most frequent chronic illness; it affects 1 individual in 6. CRS affects 75% of asthmatics and 50% of people ill with CRS are asthmatics according to the National Center for Health Statistics.

A breathing difficulty can also be observed in cases of septum deviation, asthma, pregnancy and in children.

Sportsmen at full stretch also suffer from insufficient nasal inspiration to satisfy their oxygen consumption. Snoring is also a worrying symptom of breathing difficulty. Transitory or constant mouth breathing is a symptom of insufficient nasal breathing.

The chemical and surgical solutions and the devices that exist on the market have major disadvantages. Frequent prescriptions of antibiotics are controversial through their absence of statistically significant advantages in the treatment of presumed bacterial rhinosinusitis.

Sprays of vasoconstrictors and of corticosteroids cause a secondary inflammation and are harmful to the nasal mucus; secondary congestion encourages patients to continue the use of the sprays with the risk of medicinal rhinitis and atrophy of the nasal mucus. The sometimes essential surgical solutions are invasive, like any surgical intervention, and costly. In addition they do not always give the expected results.

Nasal dilators and nasal supports are a noninvasive alternative to the chemical and surgical solutions.

Nasal supports as described for example in U.S. Pat. No. 5,922,006 or US-A-2002/0177871 do not part the nostrils and simply prevent the collapse of the nasal partitions by supporting them.

U.S. Pat. No. 1,034,123 describes a mechanical nasal dilator comprising a frame consisting of an elastic cable whereof the elasticity of the central extranasal portion pinches the top portion of the nasal ridge situated between the eyes, then, based on a loop which corresponds to the pinching point, comprises lower branches which, on the contrary, part the nostrils. In other words, one portion, the central portion, of the extranasal portion of the frame pinches the nostrils while another portion, a lateral portion, parts them. These lower branches comprise a frame extended by an arc of a circle that only very slightly enters the nostrils and comprises a pressure pad.

US 2002/000227 A and WO 00/66048 describe a mechanical nasal dilator bonded to the outside of the nose. The former is totally external to the nose and exerts its effect in the middle of the nose, while the latter comprises a tongue that is slightly inserted into the nose and, from a fixed point formed by the bonding of its upper end, pulls the entrance of the nostrils forward.

The most common device currently is a mechanical nasal dilator bonded to the outside of the nose comprising an extranasal adhesive strip, bonded to the outside of the nostrils, marketed under the name BreatheRight®, which slightly increases the nasal breathing flow. However, a bonded mechanical nasal dilator like BreatheRight® cannot be reused; it does not bond to damp or greasy skin. Made of latex, people allergic to latex cannot use it. It is inconvenient for blowing the nose and it does not really reduce snoring because it does not fulfill its first function of sufficiently increasing the nasal breathing flow.

Another nasal dilator device is marketed under the name of Nozovent®. It is a flexible device inserted into the nose that parts the nostrils. Its "U" shape and the position of its frame under the nose lead to a resultant of the exerted forces (the parting force on the inner face of the side walls due to the device, and the reaction of the side walls of the nostrils), directed toward the outside of the nose. To remedy this and prevent its spontaneous expulsion, Nozovent® is furnished with protuberances on the end plates of the device to clamp the device to the intranasal side walls of the nostrils. They may therefore be a source of friction and irritation of the intranasal skin. The device obstructs the entrance of the nostrils where touching actions are frequent. This is why many users remove it unconsciously during their sleep. In the event of an impact, Nozovent® may be pushed far into the nostrils and therefore presents a degree of risk.

It would therefore be desirable to have a practical and effective nasal dilator that is simple to produce, well supported and secure.

After lengthy research, the applicant has perfected such a nasal dilator.

SUMMARY OF THE INVENTION

That is why the subject of the present application is a mechanical nasal dilator comprising a frame furnished with pressure plates at its ends, the frame comprising a central extranasal portion and two intranasal portions, characterized in that the extranasal portion of the frame is generally U-shaped, whereof the central portion is elastic and parts the alas of the nose by spring effect, the end of each of the branches of the U itself being U-shaped whereof one branch is a portion of the extranasal portion of the frame and the other branch, situated between the branches of the extranasal portion of the frame, forms one of the aforementioned intranasal portions.

In preferable conditions of embodiment of the invention, the length of an intranasal portion of the frame lies between 0.5 and 1.5, preferably lying between 0.6 and 1.4, particularly lying between 0.7 and 1.3, more particularly lying between 0.8 and 1.2 cm.

In yet other preferred conditions of embodiment of the invention, the frame forms a continuous line formed of straight line segments and curves, that includes no closed loop.

In other preferred conditions of embodiment of the invention, the frame is furnished with pressure plates at its ends. The latter may be made in one piece with the frame. They are preferably distinct pieces in the manner of most spectacle nose plates. They are installed at the end of the frame between the U-shaped end branches.

The pressure plates especially have the shape of a thin disk 6 to 10 mm in diameter and approximately 1 mm thick. Preferably they have a convex shape in contact with the intranasal skin.

They are advantageously arranged, also like most spectacle nose plates, in order to articulate freely to adapt to the intranasal surface of the side walls of the nostrils and comprise for this purpose advantageously a multidirectional pivot or are mounted on such a pivot.

This articulation is advantageously obtained thanks to a tapering of the end of each of the branches of the U, directed toward the outside of the extranasal portion of the frame and forming pivots. These tapers are then preferably arranged approximately perpendicular to the intranasal branch. The flexibility of the material at the location of the tapers is sufficient to confer the desired freedom of articulation. A normal device for spectacles may also be used such as a cup into which a stud provided on the plates is inserted, said stud being furnished with an eye traversed by a screw or similar element also passing through the cup.

The length of an intranasal portion is advantageously such that the pressure plates rest beyond the ostium internum.

In yet other preferred conditions of embodiment of the invention, the central extranasal portion is doubly bent symmetrically. Seen from the side, this central portion therefore is generally chair-shaped.

In a preferred configuration, the angle thus formed is preferably approximately 90°, like a chair, but may take values lying between 45° and 135°, preferably lying between 57° and 123°, particularly lying between 68° and 112°, most particularly lying between 80° and 100°.

In another preferred configuration, the angle thus formed is preferably approximately 120°, like an easy chair, but may take the values lying between 75° and 165°, preferably lying between 87° and 153°, particularly lying between 98° and 144°, most particularly lying between 110° and 130°.

The central extranasal portion may be substantially rigid. But this requires parting the nostrils to install the nasal dilator. That is why in yet other preferred conditions of embodiment of the invention, the central extranasal portion is made of a material that is elastic and advantageously ultralight.

To install the nasal dilator, it is then sufficient to press laterally on the branches, to insert the nasal side walls between the U-shaped end branches and to release the pressure. The elasticity of the central extranasal portion parts the alas of the nose by spring effect and the pressure plates, in the articulated version, closely follow the shapes of the intranasal skin.

On the other hand, in U.S. Pat. No. 1,034,123 whose central extranasal portion pinches the nasal ridge, because the central branches of the U are brought closer together and because of the elasticity of said central extranasal portion, it is necessary first not to press but to part the branches laterally in the central extranasal portion, then secondly release them to attach, by pinching, the device to the nose, then squeeze up the distal portions of the branches to fourthly insert them into the entrance of the nostrils, in order fifthly and finally to release them.

In the nasal dilator that is the subject of the present invention, the central extranasal portion is in the middle of the central extranasal portion against the nasal ridge, unlike Nozovent® whose most comparable portion is situated under the nose.

In yet other preferred conditions of embodiment of the invention, the frame is made of a shape-memory metal alloy (a nonpolymer) that is advantageously biocompatible such as nickel-titanium (NiTi) or titanium-molybdenum (TiMo). The frame particularly has the shape of a metal alloy wire or cable.

The mechanical qualities of titanium alloys make it possible to produce a very thin and light frame. Titanium-molybdenum and/or nickel-titanium have a very high superelasticity which renders the device of the invention truly reusable. TiMo or NiTi allow easy management of the forces exerted via their degree of flexibility that can be varied at will. They also make it possible to vary the cross section of the frame (for example from 0.5 to 2 mm) according to the various zones of the device (central portion, curves, etc.). So the forces exerted at different degrees of flexing of the device (according to the variable dimensions of noses) on the alas of the nose may remain relatively constant. Three different sizes of the device of the invention may however satisfy the anatomic variations of the nose in individuals.

The frame is advantageously covered at least partly with a biocompatible material such as a preferably surgical category silicone.

In yet other preferred conditions of embodiment of the invention, the pressure plates are used or arranged to deliver an active ingredient associated or juxtaposed with said pressure plates.

For this it is possible to use impregnated pressure plates or cover the surface of the plates in contact with the intranasal skin with the aid of such an active ingredient where necessary associated with a base, particularly an adhesive base.

It is possible where necessary to deposit a small quantity of gel for example containing xylocaine in addition to lubricating components on the surface of the plates in contact with the intranasal skin to reduce possible irritation and anesthetize the effect of the initial pressure. The lubricant will preferably be an antisnoring oil.

The pressure plates may release medicinal products with a volatile base contained between the frame and the silicone envelope. Each flexion of the device may cause the medicinal product to flow. The medicinal product advantageously has a boiling point lower than the temperature of the nasal cavity, particularly lying between the ambient temperature and the temperature of the nasal cavity. The vaporization of the product will thus be limited to the periods of use.

The progressive intranasal medicinal release has certain advantages relative to the sprays and other actions that are not sustained over time and allows a constant local concentration of products without an initial peak. The absorbent qualities of the nasal mucus and the possibility of a very progressive and continuous release, including during sleep, open up an alternative route to all sorts of therapies.

The combination of features that defines the nasal dilator that is the subject of the present invention confers very worthwhile properties on the latter. The two ends of the dilator, placed against the inner face of the nasal side walls, part the latter by spring effect, cause a reversible widening of the anterior nasal cavity and prevent the collapse of the nasal side walls during inspiration. Consequently, the nasal dilator that is the subject of the present invention improves breathing by reducing nasal respiratory resistance and increasing the air flow through the nasal cavities.

The considerable increase in the intranasal cross section reduces the speed of the inspired air while increasing the flow of inspired air, thus minimizing turbulent flow and snoring.

An original feature of the nasal dilator that is the subject of the present invention is the installation of its center of flexion (that is the middle of the central extranasal portion) above the nostrils and particularly against the nasal ridge, which creates a reaction force of the nose. The resultant of all the forces exerted on the device is thus a force tending to cause the nasal dilator that is the subject of the present invention to enter the nose. This movement is limited by the web of the U-shaped end portions since the alas of the nose are sandwiched by this end portion of the dilator and butt against the web of the U. It does not pinch the nose and the only pressure it exerts is the parting of the nostrils. The obstruction it can cause is therefore limited.

The device does not require the pressure plates to rub on the intranasal skin to be effective, which renders the presence of protuberances unnecessary and makes it possible to cover the pressure plates with a smooth, well tolerated surface.

The nasal dilator that is the subject of the present invention does not require an adhesive to fulfill its function. However, in certain circumstances, an adhesive may be used to totally prevent, if desired, the central extranasal portion from separating from the surface of the nose.

These properties in particular justify the nasal dilator described hereinabove being used by all individuals desiring to increase their nasal breathing to remedy any inadequacy, transient or constant, both for everyday life and for sport.

Finally, the object of the present application is the use of a nasal dilator of the present invention to increase the nasal breathing of an individual or of a mammal such as a member of the horse family.

For this purpose, a mammal, particularly an individual, is furnished with a nasal dilator of the present invention as indicated hereinabove.

BRIEF DESCRIPTION OF THE DRAWINGS

The invention will be better understood if reference is made to the appended drawings in which.

DETAILED DESCRIPTION OF THE PREFERRED EMBODIMENTS

Figure 1:
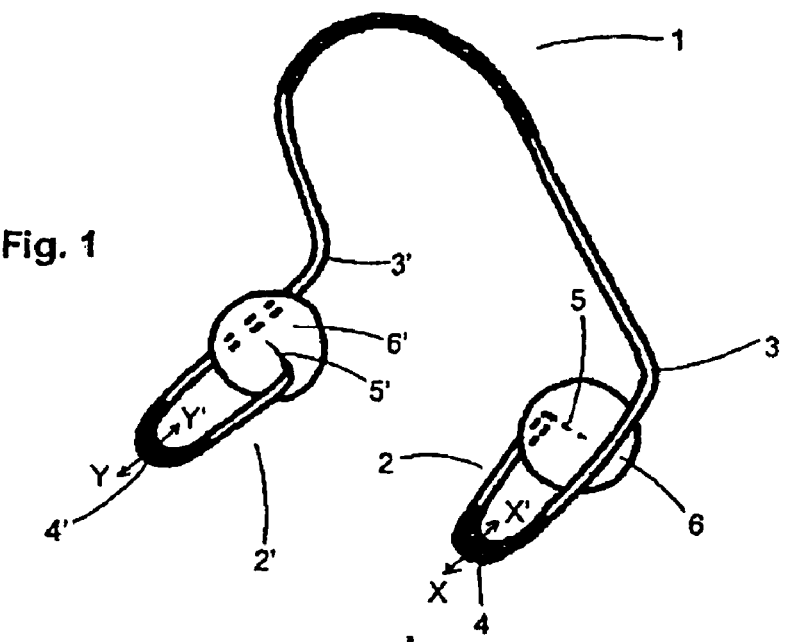
FIG. 1 represents a view in perspective of a nasal dilator

FIG. 1 shows that the nasal dilator comprises a frame that is in the form of a wire comprising seven bends. This frame may be subdivided into three portions, delimited by XX' and YY'. The frame of the embodiment shown here forms a continuous line formed of six straight line segments and five curves.

The nasal dilator comprises a bent central extranasal portion 1 (extranasal because, once installed, it will rest on the outside of the nose) and two intranasal portions 2 and 2'.

The extranasal portion 1 situated between XX' and YY' is generally U-shaped, bent into a gentle curve, and comprises a central portion delimited by two bends 3 and 3' of approximately 120° each followed by a short branch which give thereto a general shape of a chair seat and back. The extranasal portion is followed by two other hairpin bends 4, 4' that thus each form a U, bends from which the two intranasal portions 2 and 2' of the device begin.

The two ends 5 and 5' of the two intranasal portions are progressively narrowed and curved at approximately 90° in the direction of the other branch of the U. They comprise at their ends a pressure plate 6 and 6' made of the same material as the frame. This pressure plate is advantageously covered with a silicone material.

The narrowing of the cross section of the frame at this level 5, 5' creates a multidirectional articulation which allows the plate to tilt in almost all directions, thereby allowing it to adapt to the intranasal morphology of its user.

The curves of the bends 4, 4' closely following the alas of the nose prevent the pressure plates from accidentally entering further into the nostrils than intended and prevent the plates from coming into contact with the deeper and more sensitive nasal mucus. The pressure plates will therefore always remain beyond the ostium internum. At the mid-level, the frame of the embodiment shown here has a diameter greater than that of the other portions of the frame and is covered with a layer of silicones softening its contact with the alas of the nose, which it grips lightly to improve retention of the device.

Figure 2:
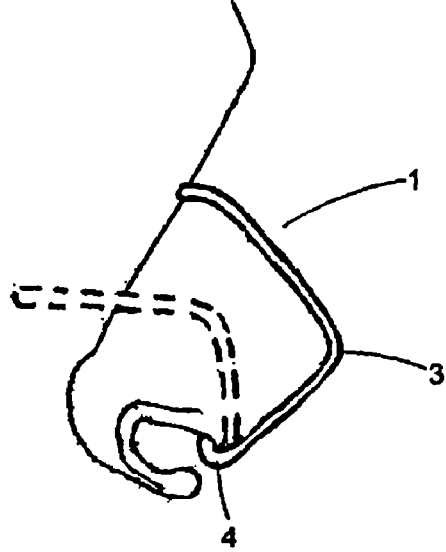
FIG. 2 represents a view in profile of a nasal dilator installed on the nose

In FIG. 2, the device is placed in a functional position on the nose. The dashed portion represents the most practical manner of installing the device on the nose. When the plates are pressing on the intranasal skin, the frame is tilted toward the back of the head to cause the mid-portion of the frame to rest on the nose. In this figure, it is not possible to distinguish the intranasal portions 2 and 2' inserted into the nostrils. On the other hand, one of the side bends 3 of the extranasal portion 1 and an ala of the nose sandwiched between the extranasal portion 1 and the corresponding intranasal portion 2 are clearly distinguishable. Observe also the abutting position of the bottom of the U-shaped end branches of the frame, at the curve 4 against the ala of the nose.

Figure 3:
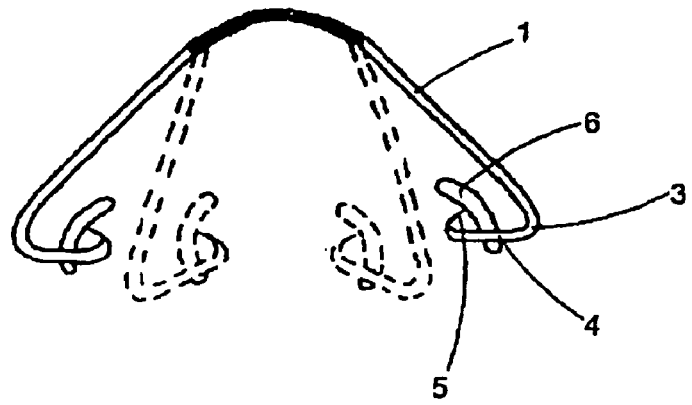
FIG. 3 represents a front view of a nasal dilator of the invention.

In FIG. 3, the drawing in dashed line represents the device bent in the position for insertion into the nose. For this, all that is required is to press the device laterally, for example between the thumb and the index finger. The drawing in solid line represents the device in the functional position, parting the alas of the nose, when the user has released the lateral pressure after having inserted the device into the nose. The angle between the U-shaped branches of the mid-portion 1 at rest is approximately 100° as can be seen.

It is again possible to see in this figure practically all the elements of FIG. 1, except for the bends 2 and 2' supported by the extranasal portion and the extranasal portion lying between the bends 3, 3' and 4, 4'.

Producing a nasal dilator of the invention in one piece, simply fully covered with a layer of silicones, makes its industrial manufacture easier.

A greater thickness of the layer of silicones on certain zones such as the pressure plates, the mid-portion or certain curves makes them soft.

The mid-portion of the extranasal segment 1 of the device may, if necessary, be provided with an adhesive surface for intensive sporting use. However, preference goes to a nonadhesive mid-portion, attached with the aid of double-sided adhesive tape, independent of the device.

The average size of the device is preferably as follows, for a frame made of TiMo or NiTi with an average diameter of 1 mm, designed for an adult man of 1.80 m:

| | |
|---|---|
| Length between the mid-portion and the bend 3, 3' | 3 cm |
| Length between the bend 3, 3' and the bend 4, 4' | 2 cm |
| Gap between the U-shaped end branches 4, 4' | 1 cm |
| Length of an intranasal portion | 1 cm |
| Diameter of circular-shaped pressure plates | 8 mm |
| Thickness of pressure plates | 1 mm |
| Angle between the U-shaped branches of the mid-portion | 100° |

The invention claimed is:

1. A mechanical nasal dilator comprising a frame furnished with pressure plates at its ends, the frame comprising an extranasal portion and two intranasal portions, wherein the extranasal portion comprises a curved central portion lying substantially in a first plane, wherein said central portion is elastic and parts the alas of the nose by spring effect, said central portion terminating at each end in a respective first bend, each first bend joining a respective end of said curved central portion to a respective one of two extranasal branches, each of said two extranasal branches lying substantially in a second plane that is not parallel to said first plane and being joined to a corresponding one of said two intranasal portions by a respective second bend, each of said intranasal portions comprising a respective one of said pressure plates, and wherein the frame includes no closed loop.

2. The nasal dilator as claimed in claim 1, wherein each of said two intranasal portions has a length from 0.5 cm to 1.5 cm.

3. The nasal dilator as claimed in claim 1, wherein the pressure plates comprise a multidirectional articulation which allows the plates to tilt or are mounted on such an articulation.

4. The nasal dilator as claimed in claim 3, wherein the multidirectional articulation is defined by a progressively narrowing of the end of each of the two intransal portions, directed toward the extranasal portion of the frame.

5. The nasal dilator as claimed in claim 1, wherein each first bend makes an angle lying between 75° and 165°.

6. The nasal dilator as claimed in claim 1, wherein the frame is made of a flexible, shape-memory metal alloy.

7. The nasal dilator as claimed in claim 6, wherein the flexible, shape-memory metal alloy is nickel-titanium or titanium-molybdenum.

8. The nasal dilator as claimed in claim 1, wherein the frame is covered at least partly with a biocompatible material.

9. The nasal dilator as claimed in claim 8, wherein the biocompatible material is a silicone or polyurethane.

10. The nasal dilator as claimed in claim 1, wherein the pressure plates are adapted to deliver an active ingredient associated or juxtaposed with said pressure plates.

11. The nasal dilator according to claim 1, wherein said frame in an unbiased state has a greater extent along a line passing through said first bends that in a direction perpendicular thereto.

12. The nasal dilator according to claim 1, wherein said frame comprises a single resilient wire.

13. The nasal dilator according to claim 3, wherein said frame has a plane of symmetry bisecting said curved central portion, and wherein said frame in an unbiased state has a greater extent in a direction perpendicular to said plane of symmetry than in a direction parallel to said plane of symmetry.

* * * * *